United States Patent [19]
Gate et al.

[11] Patent Number: 5,128,606
[45] Date of Patent: Jul. 7, 1992

[54] ASPECT RADIO MEASUREMENT

[75] Inventors: Leonard F. Gate; Terence W. Webb, both of Cronwall, United Kingdom

[73] Assignee: ECC International Limited, United Kingdom

[21] Appl. No.: 643,840

[22] Filed: Jan. 22, 1991

[30] Foreign Application Priority Data

Feb. 22, 1990 [GB] United Kingdom ............... 9001427

[51] Int. Cl.⁵ .................... G01N 15/02; G01N 27/00
[52] U.S. Cl. .................. 324/71.4; 324/439; 137/5; 73/861.08; 73/61.41
[58] Field of Search ............ 137/5; 73/61 R, 861.08; 324/71.4, 439, 699, 716

[56] References Cited

U.S. PATENT DOCUMENTS

| | | | |
|---|---|---|---|
| 3,870,065 | 3/1975 | Minns | 137/5 |
| 4,420,720 | 12/1983 | Newton | 324/71.4 |
| 4,434,398 | 2/1984 | Berg | 324/71.4 |
| 4,525,666 | 6/1985 | Groves | 324/71.4 |
| 4,778,657 | 10/1988 | Spohr | 324/71.4 |
| 4,906,936 | 3/1990 | Butas | 324/71.4 |

OTHER PUBLICATIONS

M. J. Honeywood, "Acoustically Induced Birefringence in Rigid Particle Suspensions", PhD. Thesis, University of Reading, 1989.
H. H. Trimm, B. R. Jennings & K. Parslow, "Colloid Deflocculation Detection by Transient Light Scattering", Colloids and Surfaces, 18, 113–121 (1986).
J. V. Champion, D. Downer, G. H. Meeten & L. F. Gate, "Measurement of Magnetically Induced Linear Optical Birefringence and Dichroism in Colloidal Dispersions", J. Physics E.: Scientific Instruments, vol. 10, 1137–41 (1977).
J. V. Champion, G. H. Meeten, B. R. Moon & L. F. Gate, "Optical Extinction of Randomly Oriented and Shear Flow Orientated Colloidal Kaolinite Particles", J. Chem. Soc., Fara. Trans. II, vol. 75, 780–9 (1979).

*Primary Examiner*—Kenneth A. Wieder
*Assistant Examiner*—Jose M. Solis
*Attorney, Agent, or Firm*—Klauber & Jackson

[57] ABSTRACT

A method and apparatus are disclosed for obtaining a measurement indicative of the aspect ratio of non-spherical particles in suspension. Conductivity of the suspension is measured for two different orientations of the particles between measuring points and the difference between the conductivities measured is used as an indication of the particle aspect ratio. The particle orientation will be aligned in one measurement and in the other may be aligned and transverse to the first orientation direction or random. Alternatively, there may be a single aligned orientation but transversely directed conductivity measurements.

15 Claims, 3 Drawing Sheets

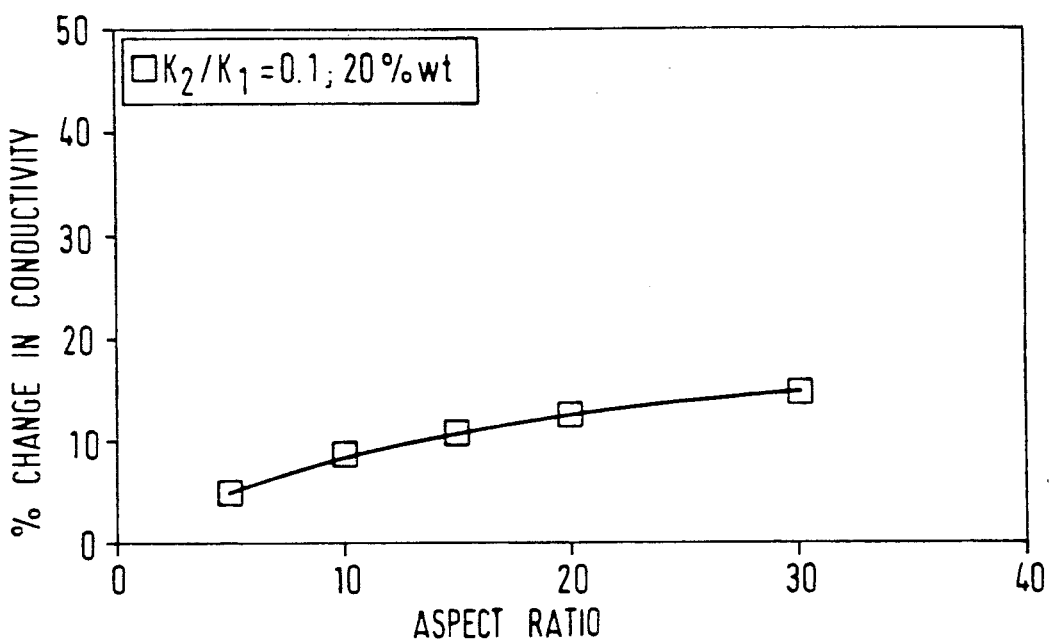
CALCULATED VALUES FOR ΔK WITH PARTICLE CONDUCTIVITY
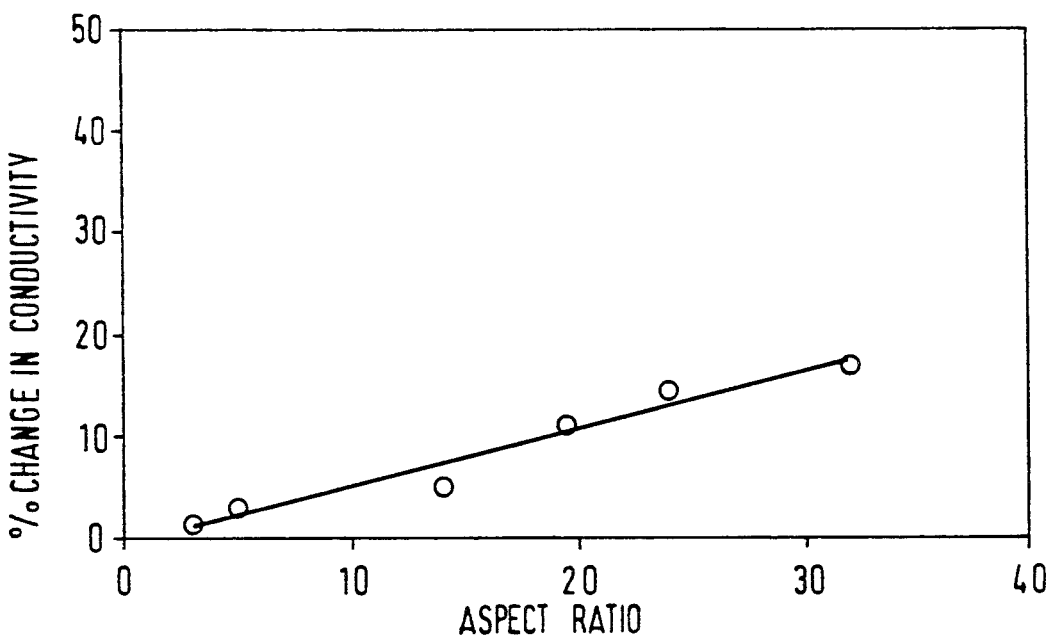
MEASURED VALUES OF ΔK IN SUSPENSIONS AT 20WT% SOLIDS THE EFFECT ON K OF BLENDING KAOLIN (DISC SHAPED PARTICLES) WITH GROUND MARBLE (NEARLY SPHERICAL PARTICLES) FOR 20% WT SUSPENSIONS.

ASPECT RADIO MEASUREMENT

The present invention relates in general to the measurement of the average aspect ratio of non-spherical, e.g. platelet-like, particles in a suspension and in particular, although not exclusively to the measurement of the aspect ratio of kaolin particles in suspension in a fluid.

Some industrial processers using particulate material may require that the particulate material has a certain average particle aspect ratio so as to achieve a desired performance characteristic from the production process. For example, in a paper coating process using kaolin particles in aqueous suspension the surface finish on the paper is determined by the average particle aspect ratio of the kaolin particles in the suspension. Different average aspect ratios will produce different paper surface finishes. If the paper manufacturer requires a smooth glossy surface, the aspect ratio will be significantly different from that required to produce a matt, more ink-absorbent, surface. By the expression "aspect ratio" of a particle as used with reference to platelet-like particles, e.g. for paper processing, is meant "the diameter of a circle of area equivalent to that of the face of a particle relative to the mean thickness of that particle". This is illustrated in FIG. 5 of the accompanying drawings. In this figure a kaolin particle P is shown with a superimposed circle having an area equivalent to that of the face of the particle. The diameter of that circle is d, the thickness of the particle is t and the aspect ratio of the particle is d/t.

A simple and inexpensive method of measuring the aspect ratio of kaolin particles during production would be extremely advantageous. In the past the aspect ratios of production have been determined using electron-micrographs. Electron-micrographs are, however, both expensive and time consuming to make. For example to carry out 10 such electron-micrographs may take a day and a half using highly experienced and skilled staff at a present day cost of approximately 60 per electron-micrograph.

For other processes a different aspect ratio may be under consideration from the aspect ratio mentioned above related to paper coating. For example, if the process uses particles of needle-like structure the aspect ratio could be the length of the particle divided by the average diameter of the particle. A general definition of what is meant by the term "aspect ratio" in relation to a particle could thus be given as being the ratio of the mean major to the mean minor dimension of the particle. What is the relevant mean major dimension and what is the relevant mean minor dimension may differ for the different type of particles, as indicated above. In the case of the kaolin particles, and for example also for similar particles such as mica or talc, the major dimension is the diameter of the circle of equivalent area and the minor dimension is the thickness of the particle. In the case of needle-like particles the major dimension is the length of the needle-like particle and the minor dimension is the diameter of the needle-like particle.

The present invention seeks to provide a method, of measuring or providing a comparative indication of the average aspect ratio of non-spherical particles, which is simple and of adequate accuracy when compared, for example, with the above-mentioned electron-micrograph method. The absolute value of aspect ratio may not be measured or measurable but the arrangement may simply be used to provide a comparative measurement or for production of a control signal used in a production process.

According to a first aspect of the present invention there is provided a method of obtaining a measure of the average aspect ratio of non-spherical particles comprising the steps of:

obtaining a fully-deflocculated suspension of the particles;

taking a first conductivity measurement of the particle suspension with the particles having one form of orientation between points of measurement of the conductivity;

taking a second conductivity measurement of the particle suspension with the particles having a form of orientation, different from said one form, between points of measurement of the conductivity; and using the difference in the two conductivity measurements as a measure of the average aspect ratio of the particles in suspension.

To provide said one form of orientation and to provide said different form of orientation it would be possible to measure the conductivity between the same two points in each step and to change the orientation of the particles between the points in each of the conductivity measuring steps.

In one step the particles could be orientated in a particular direction and in the other step the particles could be orientated in a transverse direction or alternatively allowed to take up random orientation under Brownian motion.

Orientation could be effected by applying a field to the suspension.

The same effect could be achieved by keeping the orientation of the particles in one direction but measuring conductivity between two pairs of points in transverse directions.

According to a second aspect of the present invention there is provided a method of determining the average aspect ratio of non-spherical shaped particles comprising the steps of:

producing a fully-deflocculated suspension of the particles;

orienting the particles in the suspension and measuring the conductivity of the oriented particle suspension;

allowing the particles to become randomly oriented and measuring the conductivity of the randomly oriented particle suspension; and using the difference in the two conductivity measurements to determine the average aspect ratio of the particles in the suspension.

According to a third aspect of the present invention there is provided a method of providing a parameter indicative of the weight average aspect ratio of non-spherical shaped particles comprising the steps of:

producing a fully-deflocculated suspension of the particles;

orienting the particles in the suspension and measuring the conductivity of the oriented particle suspension;

allowing the particles to become randomly oriented and measuring the conductivity of the randomly oriented particle suspension; and using the difference in the two conductivity measurements as a parameter indicating the average aspect ratio of the particles in the suspension.

The method seeks to provide a method of comparing the average aspect ratios of different samples of non-spherical particles for comparison of different samples of the particles in suspension and which can provide an indication of the suitability of the average aspect ratio measurement for a particular use. In other words the result may be used to check the suitability of a particle sample for, or to control blending of different materials to achieve a suitable sample for, use in a particular process.

The measurement method has proved particularly useful when applied to kaolin particles and at present the preferred method of orienting the particles is to apply a shear field to the particles by providing flow in the suspension used for the conductivity measurement. The shear may be transverse or longitudinal to the direction of flow. Ceasing flow of the suspension causes the particles to settle under Brownian motion into a random orientation after a period of time and the second conductivity measurement is taken after the lapse of such a period of time following the cessation of flow. Fields other than flow shear fields can be applied to the particles in suspension to effect their orientation. For example electric or magnetic fields or an acoustic shear field may be used.

For a better understanding of the present invention and the way in which it may be carried into effect reference will now be made, by way of example, to the accompanying drawings in which:

FIG. 2 shows a curve for calculated values of change in conductivity between flowing and non flowing particle suspensions with differing particle aspect ratios;

FIG. 3 shows measured values of percentage change in conductivity between flowing and non-flowing particle suspension for different particle aspect ratios;

Figure 1:
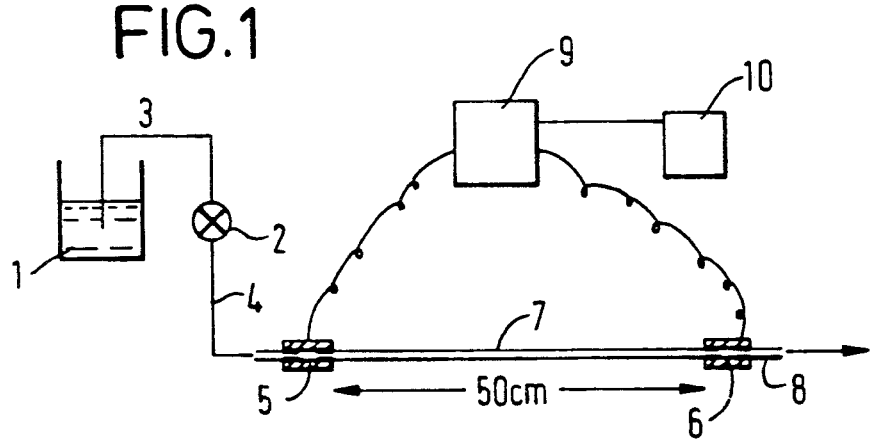
FIG. 1 shows apparatus for use in the method of determining aspect ratio according to the invention.

FIG. 1 shows in diagrammatic form an apparatus for measuring the conductivity of a suspension under flowing and non-flowing conditions in a tube. The apparatus comprises a reservoir 1 of particles in suspension. A peristaltic pump 2 is connected by an input pipe 3 to the reservoir and by an output pipe 4 to a conductivity measuring section, formed by two carbon electrodes 5 and 6, each having a bore therethrough, and a non-conductive tube 7 interconnecting the bores in the two electrodes. The pipe 4 is tightly fitted into the opposite end of the bore of carbon electrode 5 from the pipe 7, with a gap being left between the ends of the pipes 4 and 7. Similarly an output pipe 8 for the suspension is a tight fit in the opposite end of the bore of electrode 6 from the pipe 7 and, again, the ends of pipes 7 and 8 are spaced apart inside the bore in the electrode.

An electrical connection is made from each carbon electrode 5 and 6 to a conductivity meter 9 which in turn feeds an output to a chart recorder 10.

In operation the suspension in the reservoir 1 is kept in a regularly stirred state with sufficient de-flocculant added to ensure that the suspension is completely de-flocculated. The peristaltic pump is used to pump suspension from the reservoir 1 through the measuring section of the apparatus comprising the electrodes 5 and 6 and non-conductive tube 7. Using the conductivity meter 9 the conductivity of the suspension in the tube is measured and the result recorded on the chart recorder 10. Conductivity measurements of the suspension in the tube are taken with the pump operating and with the pump off. The measurement of conductivity in the absence of flow is taken a sufficient time after cessation of flow to allow for the particles to settle and assume by Brownian motion a random orientation in the suspension.

Whilst the invention is not dependent upon the accuracy or otherwise of the theory now to be advanced it is believed that the following theoretical derivation for the non-flowing and flowing suspension conductivity indicate how the difference in these conductivities is a measure of the average aspect ratio of the particles in suspension.

In 1924 H. Fricke (Phys. Rev. 214 PP575–587, 1924) provided a theoretical derivation of the conductivity of randomly oriented ellipsoidal particles in suspension, as set out below.

If the particles in a suspension are modelled as oblate spheroids in random orientation, then the specific conductivity per unit volume of the suspension ($K_R$) can be expressed as:

$$K_R = K_1 \frac{3 - (3 + 2(K_2/K_1) \cdot A)}{3 - \rho(3 + 2A)} \quad \text{E1}$$

where $K_1$ is the conductivity of the fluid phase
$K_2$ is the conductivity of the particles
$o$ is the fractional volume occupied by the particles
and $$A = \frac{1}{2 + 2(1 - M) \cdot (K_2/K_1 - 1)} + \frac{2}{2 + M \cdot (K_2/K_1 - 1)} \quad \text{E2}$$

where

M is a function of the particle shape.

In the case of oblate spheroids, which form the model of clay particles, M is given by:

$$M = \frac{\phi - 1/2 \cdot \sin 2\phi}{\sin^3 \phi} \quad \text{E3}$$

where $$\cos \phi = a/b = \frac{1}{AR}$$

with $2a$ = minor axis (thickness) of the particle
$2b = 2c$ = major axis (diameter) of the particle.
AR = aspect ratio (Note that the aspect ratio for kaolin particles is approximated by the ratio b/a).

In the case of non-conducting particles $K_2 = 0$ and equations E1 and E2 are significantly simplified. However, as will be discussed below, colloidal particles with a surface charge and an associated diffuse double layer will have a surface conductivity which will be equivalent to a small, finite value for $K_2$.

For the experimental configuration in FIG. 1, a flowing suspension of dispersed particles will be oriented with the particles having their minor axis of revolution (a) perpendicular to the conductivity measuring electric field and in this geometry the conductivity of the suspension of oriented particles ($K_o$) is given by:

$$K_o = K_1 \frac{1 - p(1 + 2(K_2/K_1) \cdot B)}{1 - p(1 + 2B)} \quad \text{E4}$$

where $$B = \frac{1}{2 + M(K_2/K_1 - 1)}$$

with M having the value given above in E3.

Thus the fractional change in specific conductivity on stopping the flow is given by $$\Delta K = \frac{K_o - K_R}{K_R}$$

and is a function of the shape of the suspended particles and the fractional volume they occupy in the suspension.

Measured values of the change of conductivity $\Delta K$ between flow and non-flow for one tested range of fully deflocculated kaolin particles at 20 wt.% are plotted in FIG. 2 as a function of their aspect ratios estimated from electron-micrographs. There is a near-linear increase in $\Delta K$ with aspect ratio. If the particles are assumed to be non-conducting (i.e. $K_2=0$) then the magnitude of $\Delta K$ calculated from E1 and E4 is greater by a factor of x3 than the experimental values. However, if a small conductivity value is included for the particles in the equations, close agreement with experimental values is achieved. The graph of FIG. 3 illustrates calculated values for $K_2=0.1 (K_1)$ i.e. with the particle conductivity being assumed to be a tenth of that of the suspending electrolyte as discussed below.

Mineral particles such as kaolin normally can be considered to have zero conductivity and mica, for example, is used as an electrical insulator. To account for an apparent conductivity in suspension we note that the suspended kaolin particles have a surface charge which produces an associated diffuse, but thin, double layer of charge surrounding the particles; this has a higher ionic concentration than the bulk of the suspending liquid. This thin layer (estimated as 100 A thick for the case of a $10^{-3}$ M electrolyte) will have a higher conductivity than the bulk electrolyte and will be equivalent in its effect to surface conductivity in the particles. Thus in the case of spherical particles it has been shown (James Clerk Maxwell, "A Treatise on Electricity and Magnetism" Vol. 1 P. 439—Dover; New York 1954) that the distribution of electric potential around a non-conducting particle with a conducting surface layer is similar to that around a simple conducting particle; a similar result for oblate spheroids would indicate why the assumption of particle conductivity leads to agreement with the measured $\Delta K$ values for the suspensions considered.

Figure 4:
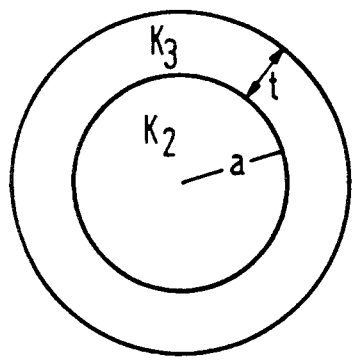
FIG. 4 is a diagrammatic representation of a particle and its equivalent surface conductance.
Figure 5:
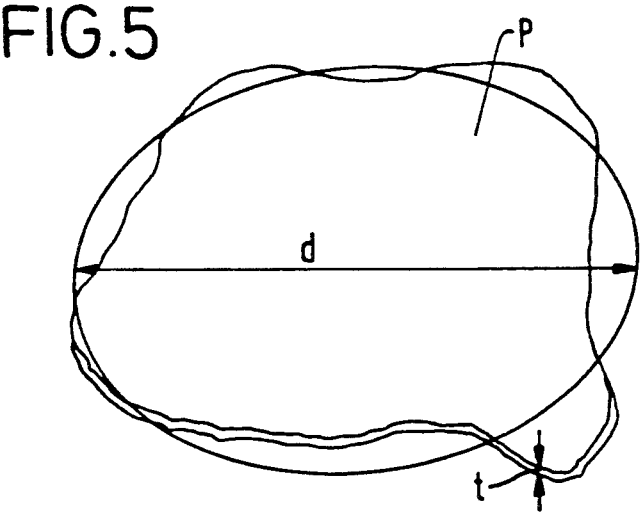
FIG. 5 shows a platelet-like particle.

The effect of surface conductance can be assessed by using the expression for spherical particles with a conducting shell given by Maxwell. In FIG. 4 there is shown a spherical particle of radius a and specific conductivity $K_2$ surrounded by a conducting shell of thickness t and specific conductivity $K_3$.

If the interior of the layered particle has zero conductivity and $t \ll a$, then the mean particle conductivity is given by:

$$K_2 = \frac{2t}{a} K_3$$

For a double-layer in a $10^{-3}$ M electrolyte $t=0.01$ μm so that for 1 μm kaolin particles the condition $t \ll a$ is met. The surface conductivity can be written as $\sigma = tK_3$ and can be obtained, for kaolin, from published experimental data. Thus in a suspending fluid with $K_1 = 51 \times 10^{-6}$ ohm$^{-1}$cm$^{-1}$) kaolin was estimated to have a surface conductivity $\sigma = 0.3 \times 10^{-9}$ (ohm$^{-1}$).

Writing $\sigma = t \times K_3 = 10^{-6} \times K_3 = 0.3 \times 10^{-9}$ ohm$^{-1}$ Then $K_3 = 0.3 \times 10^{-3}$ ohm$^{-1}$cm$^{-1}$]

Hence $K_2 = \frac{2tK_3}{a} = 6 \times 10^{-6}$ ohm$^{-1}$

We can now obtain a value for the ratio of the effective conductivity of the particle to that of the suspending fluid as:

$$\frac{K_2}{K_1} = \frac{6 \times 10^{-6}}{51 \times 10^{-6}} = 0.118$$

This is in close agreement with the value found necessary to give agreement between the experimental values of $\Delta K$ and the theory of Fricke.

Thus as can be seen from the above theory and the graphical results of FIGS. 2 and 3 the differences in conductance between the oriented particle suspension and the randomly oriented particle suspension is an acceptable measure of the average aspect ratio of the particles in the suspension. As stated the theory may be incorrect or in need of modification to take account of the shape and material of the particles being tested. However, irrespective of the accuracy, or otherwise of the theory, the method may give adequate comparative measurements of aspect ratio and measuring equipment can be initially calibrated by using known test samples of particles in suspension.

Figure 7:
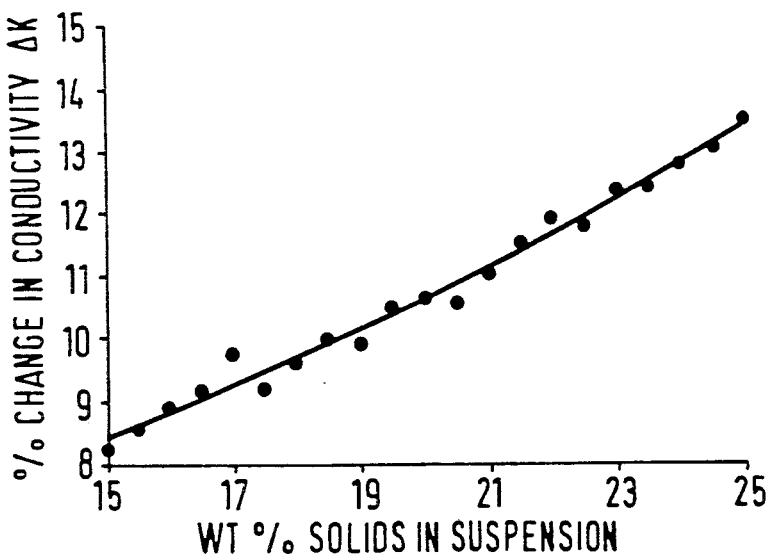
FIG. 7 shows a curve representing change in suspension conductivity for change in concentration of solids in an aqueous suspension.

When using the change in conductivity to compare the aspect ratio of particulate material it is necessary to use them in aqueous suspensions of known density or weight of suspended material per unit volume. The effect of varying the particulate solids in suspension on the percentage change in conductivity is shown in FIG. 7. It follows closely the trend indicated by the theory above. The solid line curve is the least squares polynomial approximation. The suspension concentration at which to operate this method can be chosen between a lower limit below which the percentage change in conductivity becomes too small to measure conveniently and an upper limit above which the concentration is too high for shear forces to generate a fully oriented suspension. These values will depend upon the particular nature of the particles in suspension.

Figure 6:
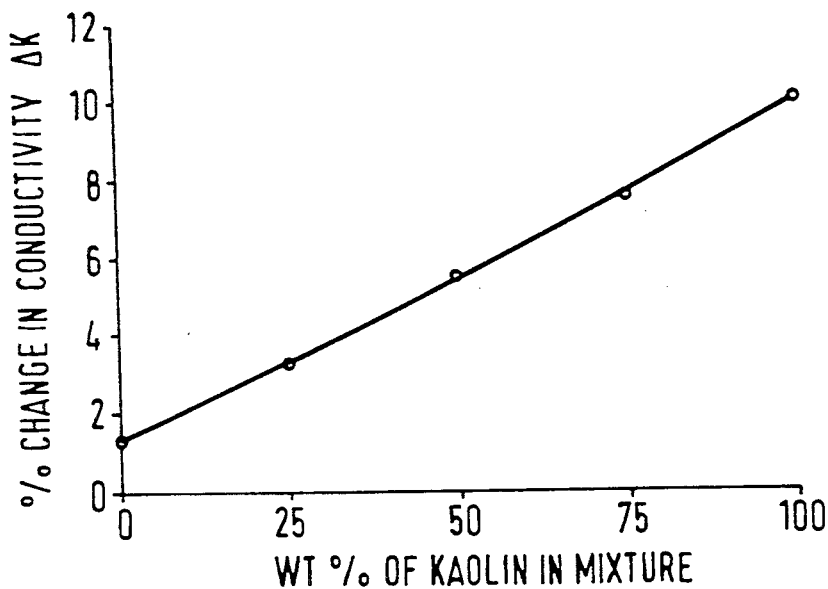
FIG. 6 shows a curve representing change in suspension conductivity for differing mixtures of kaolin and ground marble.

FIG. 6 shows a graph relating percentage change in conductivity for change in the percentage content of kaolin in a kaolin and ground marble mixture of particles in a 20% by weight of solids fluid suspension. As can be seen the percentage of kaolin varies from 0 to 100% with the ground marble content therefore varying from a 100 down to 0% in the opposite direction. The ground marble particles are nearly spherical particles and the aspect ratio is effectively 2 for such particles. Kaolin particles are platelet-like and therefore the aspect ratio increases from the value of about 2 for 0% of kaolin by weight in the mixture to the particular average aspect ratio of the pure kaolin suspension with 100% kaolin and 0% calcium carbonate. The percentage change in conductivity varies in direct proportion to the increasing average aspect ratio resulting from the increasing percentage of kaolin in the mixture. Clearly, therefore, it would be possible to use the method of measuring the percentage change in conductivity to control blending of particulate materials to achieve a desired weight average aspect ration. Whilst blending is displayed by the curve showing blending of a mixture of spherical ground marble particles with platelet-like kaolin particles, the technique can obviously and very usefully be applied to controlling the average aspect ratio of blended non-spherical particles of the same chemical nature so as to achieve a particular weight average aspect ratio of such particles. For example, kaolin of different average aspect ratios from two different sources could be blended to achieve a desired average aspect ratio for use in paper coating.

The method used for orienting the particles in suspension and thereafter producing randomly oriented particles is not significant but the shear field system of FIG. 1 is very convenient. The other methods of orientation mentioned earlier can also be used as can other methods of and apparatus for conductivity measurement.

The described process forms a very simple aspect ratio measurement or indication method which is both cheap and fast and which is sufficiently accurate for on-line production measurement and/or control.

The term "measurement" is used broadly herein to cover not only determination of the particular value but also the obtaining of an indication of the value or comparative value. In process control no external output may be given but a signal corresponding to the aspect ratio may be utilised directly for closed loop purposes.

As well as monitoring blending of particle suspensions to produce a suspension of particles of desired weight average aspect ratio, monitoring of mechanically treated particles in suspension can be carried out to determine when the mechanical treatment has produced a desired average aspect ratio.

The specific embodiment described above measures conductivity between the same points with particles oriented in one direction and then with particles randomly oriented. As mentioned, instead of using random orientation for the second conductivity measurement, by application of a suitable field, the particles could be oriented in a direction transverse to that of the first measurement. This may be effected by the application of a different type of field or of the same field but in a transverse direction to that used in the first measurement. In the described apparatus it may be convenient to apply a magnetic or electric field with no suspension flow to cause particles to orientate in a direction transverse to that caused by suspension flow.

Alternatively a single direction of particle orientation could be used with conductivity measurements being taken between two pairs of points at direction transverse one to the other.

We claim:

1. A method of obtaining a measure of the average aspect ratio of non-spherical particles comprising the steps of:
    obtaining a fully-deflocculated suspension of the particles;
    taking a first conductivity measurement of the particle suspension with the particles having one form of orientation between points of measurement of the conductivity;
    taking a second conductivity measurement of the particle suspension with the particles having a form of orientation, different from said one form, between points of measurement of the conductivity; and
    using the difference in the two conductivity measurements as a measure of the average aspect ratio of the particles in suspension.

2. A method according to claim 1 wherein said points of measurement are the same for each conductivity measurement and a field is applied to the particle suspension to cause it to take said one form of orientation.

3. A method according to claim 2 wherein a different field in a direction transverse to said field is applied to the particle suspension to cause it to take said different form of orientation.

4. A method according to claim 2 wherein said different form of orientation is random orientation achieved by allowing time for said particles to settle into random orientation under Brownian motion.

5. A method according to claim 1 wherein a field is applied to said particle suspension to cause orientation of particles in a particular direction and wherein said conductivity measurements are taken in two different directions relative to said particular direction of orientation so as to produce said one form and said different form of orientation between the points of measurement of conductivity.

6. A method of determining the average aspect ratio of non-spherical particles comprising the steps of:
    producing a fully-deflocculated suspension of the particles;
    orienting the particles in the suspension and measuring the conductivity of the oriented particle suspension;
    allowing the particles to become randomly oriented and measuring the conductivity of the randomly oriented particle suspension; and
    using the difference in the two conductivity measurements to determine the average aspect ratio of the particles in the suspension.

7. A method of providing a parameter indicative of the weight average aspect ratio of non-spherical shaped particles comprising the steps of:
    producing a fully-deflocculated suspension of the particles;
    orienting the particles in the suspension and measuring the conductivity of the oriented particle suspension;
    allowing the particles to become randomly oriented and measuring the conductivity of the randomly oriented particle suspension; and
    using the difference in the two conductivity measurements as a parameter indicating the average aspect ratio of the particles in the suspension.

8. A method of producing a fluid suspension of particles having a desired weight average aspect ratio comprising the steps of:
    producing a first fully deflocculated suspension of particles having an average aspect ratio greater than the desired aspect ratio;
    producing a second fully-deflocculated suspension of particles having a lower than desired weight average aspect ratio;

blending a quantity of one of the suspensions with the other suspension in successive steps;

after each blending step, determining the average aspect ratio of the blended suspension by taking a first conductivity measurement of the particle suspension with the particles having one form of orientation between points of measurement of the conductivity;

taking a second conductivity measurement of the particle suspension with the particle shaving a form of orientation, different from said one form, between points of measurement of the conductivity; and using the difference in the two conductivity measurements as a measure of the average aspect ratio of the particles in suspension; and repeating the blending and average aspect ratio determination steps until the determination indicates that the average aspect ratio corresponds to the desired average aspect ratio.

9. A method according to claim 6 wherein afield is applied to the suspension as the method of orienting the particles in their suspension.

10. A method according to claim 7, wherein afield is applied to the suspension as the method of orienting the particles in their suspension.

11. A method according to claim 8, wherein a field is applied to the particles in their suspension to cause them to take said one form of orientation.

12. A method according to any one of claims 2 to 5 or claim 9, 10 to 11, wherein said field or said different field is a magnetic field.

13. A method according to any one of claism 2 to 5 or claim 9, 14 or 15, wherein said field or said different field is an acoustic shear field.

14. A method according to any one of claims 2 to 5 or claim 9, 10 or 11, wherein said field or said different field is a flow shear field.

15. A method according to any one of claims 2 to 5 or claim 9, 10 or 11, wherein said field or said different field is an electric field.

* * * * *